US011944322B2

(12) United States Patent
McEwen et al.

(10) Patent No.: US 11,944,322 B2
(45) Date of Patent: Apr. 2, 2024

(54) TOURNIQUET WITH USER-SELECTABLE SAFETY PROTOCOLS

(71) Applicant: Western Clinical Engineering Ltd., Vancouver (CA)

(72) Inventors: James Allen McEwen, Vancouver (CA); Michael Jameson, North Vancouver (CA); Tom Yu Chia Lai, Vancouver (CA)

(73) Assignee: Western Clinical Engineering Ltd., Vancouver (CA)

( * ) Notice: Subject to any disclaimer, the term of this patent is extended or adjusted under 35 U.S.C. 154(b) by 692 days.

(21) Appl. No.: 17/252,704

(22) PCT Filed: Jun. 21, 2019

(86) PCT No.: PCT/IB2019/055233
§ 371 (c)(1),
(2) Date: Dec. 15, 2020

(87) PCT Pub. No.: WO2019/244111
PCT Pub. Date: Dec. 26, 2019

(65) Prior Publication Data
US 2021/0145455 A1 May 20, 2021

Related U.S. Application Data

(60) Provisional application No. 62/688,997, filed on Jun. 22, 2018.

(51) Int. Cl.
*A61B 17/00* (2006.01)
*A61B 17/135* (2006.01)
(Continued)

(52) U.S. Cl.
CPC .......... *A61B 17/1355* (2013.01); *A61B 90/08* (2016.02); *A61B 2017/00022* (2013.01);
(Continued)

(58) Field of Classification Search
CPC . A61B 17/132; A61B 17/135; A61B 17/1355; A61B 2017/00022;
(Continued)

(56) References Cited

U.S. PATENT DOCUMENTS

| 5,556,415 A | 9/1996 | McEwen et al. |
| 5,607,447 A | 3/1997 | McEwen et al. |

(Continued)

FOREIGN PATENT DOCUMENTS

| EP | 1909657 | 4/2008 |
| EP | 3166509 | 5/2017 |

(Continued)

OTHER PUBLICATIONS

Extended European Search Report for European Application No. 19822298.6, dated Jun. 14, 2021.
(Continued)

*Primary Examiner* — Katherine M Rodjom
*Assistant Examiner* — Lindsey R. Rivers
(74) *Attorney, Agent, or Firm* — Klarquist Sparkman, LLP (57) ABSTRACT

A tourniquet apparatus comprises a cuff, a user interface, a controller, a protocol hazard key and a protocol safety interlock. The cuff encircles the patient's limb and applies a level of pressure. The UI presents a protocol symbol from a plurality of protocol symbols wherein each protocol symbol is indicative of a corresponding safety protocol. The controller is responsive to stored pressure levels and stored times specified by the safety protocol, after any adjustments by the user, and operable during the stored protocol time period for maintaining the level of pressure applied by the cuff to the individual patient near the plurality of stored pressure levels at the plurality of stored times. The protocol hazard key is actuatable to end the stored protocol time
(Continued)

period while the controller is operable. The protocol safety interlock prevents selection of a second protocol symbol while the controller is operable.

19 Claims, 3 Drawing Sheets

(51) Int. Cl.
*A61B 90/00* (2016.01)
*A61B 5/00* (2006.01)
*A61B 5/022* (2006.01)
*A61B 34/00* (2016.01)
*A61B 90/90* (2016.01)

(52) U.S. Cl.
CPC .............. *A61B 2017/00115* (2013.01); *A61B 2017/00132* (2013.01); *A61B 2017/00199* (2013.01); *A61B 2090/0808* (2016.02); *A61B 2505/05* (2013.01)

(58) Field of Classification Search
CPC .......... A61B 2017/00115; A61B 2017/00199; A61B 2017/00132; A61B 90/08; A61B 2090/0808; A61B 34/25; A61B 2505/05
See application file for complete search history.

(56) References Cited

U.S. PATENT DOCUMENTS

| | | | |
|---|---|---|---|
| 5,855,589 | A | 1/1999 | McEwen et al. |
| 7,479,154 | B2 * | 1/2009 | McEwen ............. A61B 5/02233 606/202 |
| 9,039,730 | B1 | 5/2015 | McEwen et al. |
| 9,113,895 | B2 | 8/2015 | McEwen et al. |
| 9,138,236 | B2 | 9/2015 | McEwen et al. |
| 2008/0262533 | A1 * | 10/2008 | McEwen ............. A61B 17/1355 606/202 |
| 2009/0124912 | A1 * | 5/2009 | McEwen ............. A61B 5/0235 600/495 |
| 2013/0211445 | A1 * | 8/2013 | McEwen ............. A61B 17/1355 606/202 |
| 2016/0270795 | A1 * | 9/2016 | Krahwinkel ....... A61B 5/02141 |

FOREIGN PATENT DOCUMENTS

| | | | | |
|---|---|---|---|---|
| WO | WO94/22364 | 10/1994 | | |
| WO | WO2007/016772 | 2/2007 | | |
| WO | WO-2007016772 A1 * | 2/2007 | ......... | A61B 17/1322 |
| WO | WO2016/004519 | 1/2016 | | |

OTHER PUBLICATIONS

International Search Report and Written Opinion for PCT/IB2019/055233, dated Aug. 22, 2019.

Office Action for Australian Application No. 2019291640, dated May 10, 2023.

* cited by examiner

TOURNIQUET WITH USER-SELECTABLE SAFETY PROTOCOLS

CROSS REFERENCE TO RELATED APPLICATION

This is the U.S. National Stage of International Application No. PCT/IB2019/055233, filed Jun. 21, 2019, which was published in English under PCT Article 21(2), which in turn claims the benefit of U.S. Provisional Patent Application No. 62/688,997, filed Jun. 22, 2018, which are hereby incorporated by reference.

FIELD

This invention pertains to pneumatic tourniquet systems commonly used for restricting the flow of arterial blood into a portion of a patient's limb to facilitate the safe performance of a medical procedure. In particular, this invention pertains to a pneumatic tourniquet apparatus with user-selectable safety protocols, wherein each safety protocol specifies a plurality of stored pressure levels associated with a plurality of stored times to be maintained during the duration of the medical procedure for a specific individual patient. Each safety protocol further includes a protocol hazard key and a protocol safety interlock to prevent hazardous operation.

BACKGROUND

Tourniquet systems are commonly used in surgical settings to stop the penetration of arterial blood into a portion or region of a patient's extremity, thus creating a clear, dry surgical field that facilitates the performance of a surgical procedures and improves outcomes. Surgical tourniquet systems of the prior art include a tourniquet cuff for encircling a limb at a desired location, a tourniquet instrument, and flexible tubing connecting the cuff to the instrument. The tourniquet instrument contains a user interface for a user to view and adjust pressure, time and other parameters, and to initiate inflation or deflation of the tourniquet cuff. Typically, the user sets a reference pressure level and a time period suitably long for the performance of a surgical procedure. The user inflates the tourniquet cuff to the reference pressure level for the duration of the surgical procedure and deflates the tourniquet cuff at the end of the surgical procedure. Many types of such pneumatic surgical tourniquet systems have been described in the prior art, such as those described by McEwen in U.S. Pat. Nos. 4,469,099, 4,479,494, 5,439,477 and by McEwen and Jameson in U.S. Pat. Nos. 5,556,415 and 5,855,589, which are incorporated herein by reference.

There are several methods of setting the reference pressure level. Some examples are described below:

In some cases, the reference pressure level is set to a standard pressure of either 250 mmHg for upper limbs, or 350 mmHg for lower limbs. However, this method only accounts for whether the surgical procedure is performed on the upper limb or lower limb. It does not account for the physiologic characteristics of the patient, such as blood pressure or limb characteristics, which can lead to hazardous conditions. For an example, this method may lead to the user setting and applying a reference pressure level of 350 mmHg to a lower limb of a pediatric patient. Since, typically, it requires lower pressures to occlude arterial blood flow in a pediatric patient than an adult patient, this method may result in excessive applied pressure and increased risk of injury. Therefore, for surgical procedures involving pediatric patients, the reference pressure levels should be lower and more limited than ones used for adult patients.

Another method is to set the reference pressure level based on a formula. Typically, these formulas include parameters such as cuff width, the patient's systolic blood pressure and limb circumference. However, this method is complex and requires the user to perform time-consuming calculations. Furthermore, these formulas may only be applicable for a specific tourniquet cuff. Using a formula not intended for the applied cuff may lead to under-pressurization or over-pressurization resulting in bleed through or increased risk of nerve and soft tissue injuries.

Another method is to set the reference pressure level based on the patient's Limb Occlusion Pressure (LOP), as described by McEwen in U.S. Pat. No. 9,931,126. LOP can be defined as the minimum pressure required, at a specific time in a specific tourniquet cuff applied to a specific patient's limb at a specific location, to stop the flow of arterial blood into the limb distal to the cuff. LOP is affected by variables including the patient's limb characteristics, characteristics of the selected tourniquet cuff, the technique of application of the cuff to the limb, physiologic characteristics of the patient including blood pressure and limb temperature, and other clinical factors (for example, the extent of any elevation of the limb during LOP measurement and the extent of any limb movement during measurement). LOP can be measured manually using Doppler ultrasound, automatically using a distal sensor as described by McEwen in U.S. Pat. No. 9,301,701, or automatically using a dual-purpose cuff as described by McEwen in U.S. Pat. No. 9,931,126, all of which are incorporated herein by reference. The current established guideline for setting tourniquet pressure based on LOP is that an additional safety margin of pressure is added to the measured LOP, in an effort to account for variations in physiologic characteristics and other changes that may be anticipated to occur normally over the duration of a surgical procedure. However, this safety margin is generalized and does not account for requirements specific to the surgical procedure. For instance, higher safety margins may be required because of the anesthetics used or because of greater limb manipulation experienced during some surgical procedures.

In U.S. Pat. No. 9,931,126, McEwen et al. describes a surgical tourniquet system with a single channel for a single cuff. However, tourniquet systems are also commonly used with two channels for two cuffs or for a single cuff with two bladders. These multi-cuff or multi-bladder tourniquet systems are commonly used for surgeries involving intravenous regional anesthesia (IVRA) or bilateral procedures. In both cases, the reference pressure levels and times are critical to the result of the surgery and the safety of the patient.

In IVRA procedures, a dual-bladder cuff or a two-cuff system is used to retain an anesthetic agent after its introduction within a desired area. If the reference pressure levels or the inflation and deflation times of the dual-bladder cuff or a two-cuff system are not set properly, the anesthetic agent may enter the patient's circulatory system, causing serious injury or death.

For bilateral procedures, simultaneous inflation or deflation of multiple cuffs on the patient's limbs may cause undesirable systemic responses such as rapid changes in the patient's blood pressure and core temperature.

Outside of surgical settings, tourniquet systems may also be used for blood flow restriction (BFR) therapy to pre-habilitate or rehabilitate a patient's limb. Typically, the user sets a reference pressure level and a time period suitably long for the performance of a BFR therapy. Depending on the desired effect of the BFR therapy, a tourniquet cuff may be applied on an upper or lower limb, on a single limb or multiple limbs, involving one inflation time period or multiple inflation and deflation cycles, and while the patient is stationary or performing multiple sets of exercise repetitions. Similar to tourniquet systems used in surgical settings, the setting of the reference pressure levels and times are dependent on the specific BFR therapy and crucial to the safety and effectiveness of the BFR therapy.

Regardless of whether the medical procedure is for surgery or for BFR, hazardous conditions may develop if a previously-selected safety protocol is used on a different patient for a different medical procedure. For an example, if a previously-selected safety protocol for a lower-limb bariatric patient is used on a pediatric patient, excessively high pressures levels and excessive long times may be used resulting in increased risk of patient injury.

During the protocol time period, hazardous conditions may arise unrelated to the tourniquet use. It is therefore important for the tourniquet apparatus to allow the user to end the safety protocol if a hazardous situation is perceived by the user such that the tourniquet apparatus reverts to a predetermined safe pressure level and time.

Therefore, there is a need for a tourniquet system that allows the user to select a safety protocol, from a plurality of safety protocols, that is safe and effective for the duration of a specific medical procedure, such as a surgical procedure or a BFR therapy. Each safety protocol specifies a plurality of reference pressure levels associates with a plurality of times within a protocol time period to account for patient and cuff variables, and safety requirements for the specific surgical procedure or BFR therapy. Each protocol further specifies safety limits associated with the reference pressure levels and times to prevent hazardous operations by the user. Each safety protocol further includes a protocol hazard key and a protocol safety interlock to prevent hazardous operation

SUMMARY

Described below are a tourniquet apparatus and methods that address shortcomings in conventional tourniquet apparatus and methods.

According to a first implementation, a tourniquet apparatus comprises a cuff for encircling and applying a level of pressure to a limb of an individual patient, a user interface, a controller, a protocol hazard key and a protocol safety interlock. The user interface is adapted for selection by a user of a protocol symbol from a plurality of protocol symbols wherein each protocol symbol is indicative of a corresponding safety protocol that specifies a plurality of stored pressure levels associated with a plurality of stored times during a stored protocol time period. The user interface is further adapted to enable the user to adjust at least one pressure level of the plurality of stored pressure levels indicated by the selected protocol symbol within safe pressure limits associated with the selected protocol symbol. The controller is responsive to the plurality of stored pressure levels and the plurality of stored times specified by the safety protocol, after any adjustments by the user, and operable during the stored protocol time period for maintaining the level of pressure applied by the cuff to the individual patient near the plurality of stored pressure levels at the plurality of stored times. The protocol hazard key is adapted for manual actuation by the user to end the stored protocol time period at any time while the controller is operable if a hazard to the individual patient is perceived by the user. The protocol safety interlock is adapted to prevent selection of a second protocol symbol by the user while the controller is operable.

The tourniquet apparatus can further comprise a physiologic sensor adapted for sensing a level of a physiologic parameter of the individual patient, and further adapted for ending the stored protocol time period if the sensed level exceeds a predetermined threshold.

The tourniquet apparatus can further comprise a physiologic measurement apparatus adapted for measuring a Limb Occlusion Pressure of the individual patient, and wherein the protocol hazard key is further adapted for automatic actuation if the Limb Occlusion Pressure exceeds a predetermined threshold.

The tourniquet apparatus can be configured such that actuation of the protocol hazard key overrides the plurality of stored pressure levels with a predetermined pressure level. The tourniquet apparatus can be configured such that the controller further stops responding to the plurality of stored pressure levels and the plurality of stored times at the end of the stored protocol time period.

The tourniquet apparatus can be configured such that the controller further replaces the plurality of stored pressure levels with a predetermined pressure level at the end of the stored protocol time period.

The tourniquet apparatus can be configured such that the controller further replaces the plurality of stored times with a predetermined time at the end of the stored protocol time period.

The tourniquet apparatus can be configured such that the controller is further operable after the end of the stored protocol time period for maintaining the level of pressure applied by the cuff to the limb of the individual patient near a predetermined pressure level.

The protocol safety interlock can be further adapted to prevent selection of a second protocol symbol after the stored protocol time period ends while the cuff encircles the limb of the individual patient. The protocol safety interlock can prevent adjustment of any one of the plurality of stored pressure levels beyond the safe pressure limit associated with the selected protocol symbol while the controller is operable. The protocol safety interlock can prevent adjustment of any one of the plurality of times beyond the safe time limit associated with the selected protocol symbol while the controller is operable.

The user interface can be configured to display a user-perceptible indication that the safety protocol has been selected. The user-perceptible indication can be removed from the user interface at the end of the stored protocol time period.

The safety protocol can further specify that each one of the plurality of stored pressure levels is a predetermined function of a measured Limb Occlusion Pressure of the individual patient. The predetermined function of the measured Limb Occlusion Pressure of the individual patient can be a percentage thereof. The safety protocol can further specify that each one of the plurality of stored pressure levels is greater than a measured Limb Occlusion Pressure of the individual patient by a predetermined margin.

According to another implementation, a tourniquet apparatus comprises a cuff for encircling and applying a level of pressure to a limb of an individual patient, a user interface, a controller, a protocol hazard key and a protocol safety interlock. The user interface is adapted for selection by a user of a protocol symbol from a plurality of protocol symbols wherein each protocol symbol is indicative of a corresponding safety protocol that specifies a plurality of stored pressure levels associated with a plurality of stored times during a stored protocol time period. The user interface can be further adapted to enable the user to adjust at least one time of the plurality of stored times indicated by the selected protocol symbol within safe time limits associated with the selected protocol symbol. The controller can be responsive to the plurality of stored pressures levels and the plurality of stored times specified by the safety protocol, after any adjustments by the user, and operable during the stored protocol time period for maintaining the level of pressure applied by the cuff to the individual patient near the plurality of stored pressure levels at the plurality of stored times. The protocol hazard key can be adapted for manual actuation by the user to end the stored protocol time period at any time while the controller is operable if a hazard to the individual. The protocol safety interlock can be adapted to prevent selection of a second protocol symbol by the user while the controller is operable.

According to another implementation, a tourniquet apparatus comprises a cuff for encircling and applying a level of pressure to a limb of an individual patient, a user interface, a controller, a protocol hazard key, a protocol safety interlock and a patient monitor. The user interface can be adapted for selection by a user of a protocol symbol from a plurality of protocol symbols wherein each protocol symbol is indicative of a corresponding safety protocol that specifies a plurality of stored pressure levels associated with a plurality of stored times during a stored protocol time period. The user interface can be further adapted to enable the user to adjust at least one pressure level of the plurality of stored pressure levels indicated by the selected protocol symbol within safe pressure limits associated with the selected protocol symbol. The controller can be responsive to the plurality of stored pressure levels and the plurality of stored times specified by the safety protocol, after any adjustments by the user, and operable during the stored protocol time period for maintaining the level of pressure applied by the cuff to the individual patient near the plurality of stored pressure levels at the plurality of stored times. The protocol hazard key can be adapted for actuation by the user to manually end the stored protocol time period at any time while the controller is operable if a hazard to the individual patient is perceived by the user. The protocol safety interlock can be adapted to prevent selection of a second protocol symbol by the user while the controller is operable. The patient monitor can be adapted for monitoring connection of the tourniquet apparatus to the individual patient, and wherein the tourniquet apparatus is further adapted for ending the stored protocol time period if the monitored connection to the individual patient is interrupted.

The tourniquet apparatus can include a physiologic sensor adapted for sensing a level of a physiologic parameter of the individual patient, wherein the connection is monitored by monitoring the level of the physiological parameter, and wherein interruption is determined if the level falls below a stored threshold.

The foregoing and other objects, features, and advantages of the invention will become more apparent from the following detailed description, which proceeds with reference to the accompanying figures.

DETAILED DESCRIPTION OF PREFERRED EMBODIMENTS

The illustrated embodiments are not intended to be exhaustive or limit the invention to the precise form disclosed. They are chosen and described in order to explain the principles of the invention and its application and practical use, and thereby enable others skilled in the art to utilize the invention.

Figure 1:
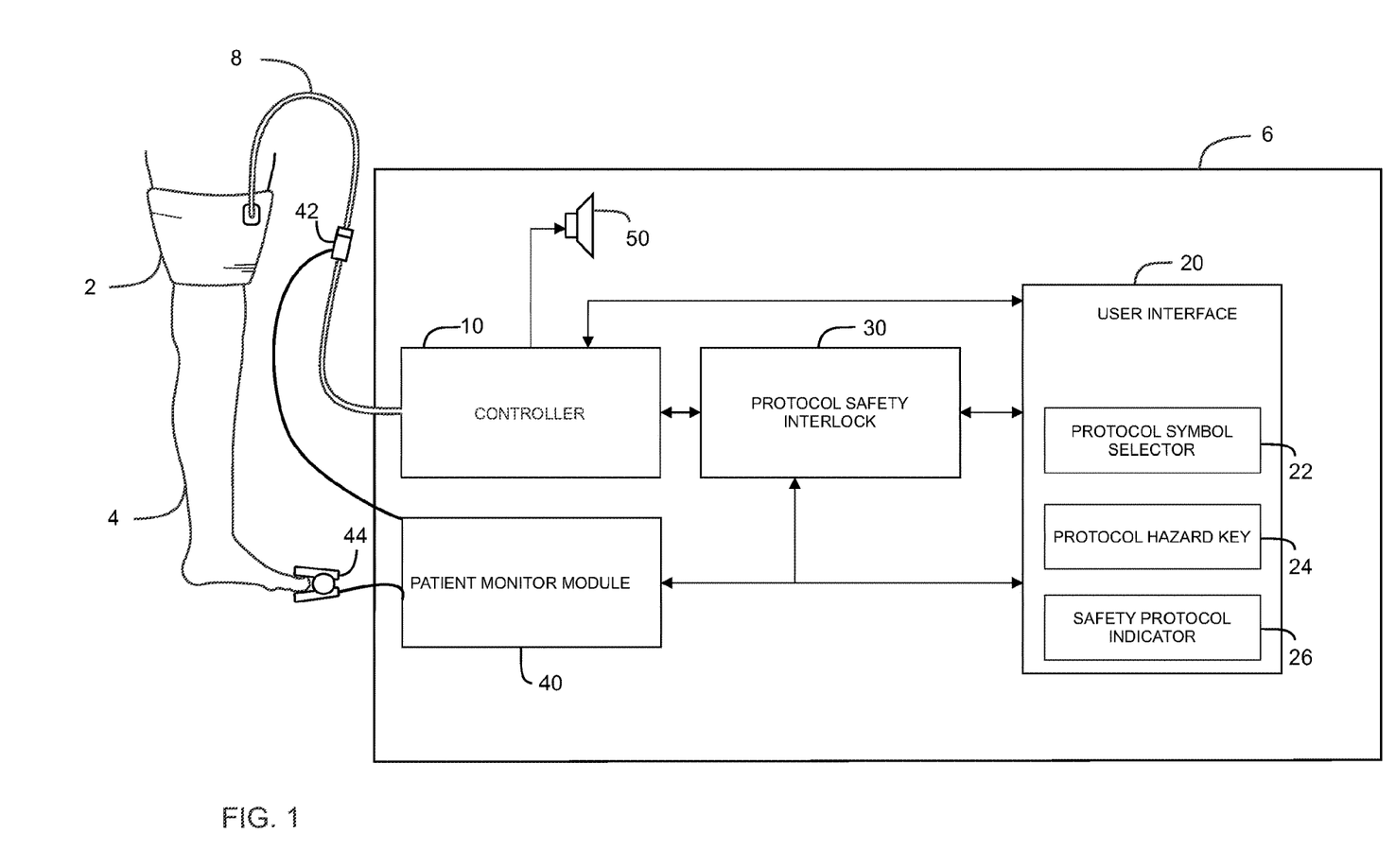
FIG. 1 is a detailed block diagram of a preferred embodiment.

FIG. 1 shows a block diagram of a tourniquet system of a preferred embodiment. Cuff 2 is shown encircling a limb of an individual patient 4 and pneumatically connected to instrument 6 through hose assembly 8. Instrument 6 comprises, controller 10, user interface 20, protocol safety interlock 30, patient monitor module 40, and speaker 50.

Controller 10 includes a pneumatic pump and valve assembly to regulate pneumatic pressure within cuff 2 near a reference pressure level.

User interface 20 communicates with controller 10 to allow a user to control the operation of instrument 6.

In the preferred embodiments, user interface 20 is an LCD graphical display with integrated touch screen, it will be appreciated that other types of user interfaces capable of receiving user input and showing symbols may be used.

User interface 20 includes protocol symbol selector 22 to allow a user to select a desired safety protocol specific to an individual patient to facilitate a medical procedure involving the patient, by touching a protocol symbol representative of the desired protocol from a selection of displayed protocol symbols. A safety protocol specifies a stored protocol time period comprising a series of stored pressure levels, with each stored pressure level associated with a stored time that the stored pressure level will be maintained for. Upon selection of a protocol symbol, protocol symbol selector 22 communicates the selected safety protocol to controller 10 through protocol safety interlock 30. Controller 10 is responsive to the safety protocol and operable for maintaining the pressure in cuff 2 near each of the stored pressure levels during the stored protocol time period.

A safety protocol may also specify safety limits associated with stored pressure levels and times. User interface 20 may permit a user to manually adjust the stored pressure levels and stored times within the safe limits specified in the safety protocol, as described further below. When a user attempts to adjust a stored pressure level or stored time beyond the associated safety limits, a visual and/or audio alert is produced by user interface 20 and speaker 50, and/or protocol safety interlock 30 prevents controller 10 from acting on adjustments beyond the associated safety limits. The protocol safety interlock 30 may be implemented through software and/or hardware.

User interface 20 further includes protocol hazard key 24 which communicates with controller 10 through protocol safety interlock 30. While controller 10 is operable, if a hazard to the individual patient is perceived by the user, the user may actuate protocol hazard key 24 to manually end the selected safety protocol by ending the stored protocol time period. It will be apparent that protocol hazard key 24 may be implemented other than as shown on user interface 20. For example, protocol hazard key 24 may be implemented as a discrete key on a remote apparatus. Controller 10 is no longer responsive to the selected safety protocol once the stored protocol time period ends. Protocol safety interlock 30 may then communicate to controller 10 to maintain the pressure in cuff 2 near a predetermined reference pressure level for a predetermined time.

While controller 10 is operable, protocol safety interlock 30 prevents selection of a second protocol symbol through protocol symbol selector 22 by the user, to prevent hazardous situation in which controller 10 follows a different, potentially inappropriate and hazardous safety protocol midway through a medical procedure for the individual patient.

Instrument 6 may include patient monitor module 40. Patient monitor module 40 is adapted for monitoring connection of the tourniquet apparatus to an individual patient and for monitoring physiologic signals of the individual patient. Patient monitor module 40 may stop the safety protocol by ending the stored protocol time period if the monitored connection to the individual patient is interrupted or if the physiologic signal is above or below a predetermined threshold.

In a preferred embodiment, patient monitor module 40 includes a cuff identification apparatus 42 carried on the connectors of hose assembly 8, as described by McEwen in U.S. Pat. No. 6,682,547, which is incorporated by reference. Cuff identification apparatus 42 can identify whether or not cuff 2 is connected to instrument 6, and the physical characteristics of cuff 2, such as its width, and length. Patient monitor module 40 communicates with user interface 20 to automatically actuate protocol hazard key 24 if cuff 2 is no longer encircling the limb of the individual patient 4. Patient monitor module 40 may further communicate with protocol safety interlock 30 to prevent selection of a second protocol symbol through protocol symbol selector 22 after the stored protocol time period ends while the cuff encircles limb of the individual patient 4. Protocol safety interlock 30 reenables the selection of a second protocol symbol once patient monitor 40 detects cuff 2 has been removed from the limb of the individual patient 4, and a second patient is connected to instrument 6. Alternatively, protocol safety interlock 30 may reenable the selection of a second protocol symbol once the user confirms the action. This prevents the user from inadvertently using the same safety protocol for the second patient, which can be inappropriate and hazardous. The plurality of pressure levels and plurality of times associated with the selected protocol symbol, and their safety limits may also be modified based on the detected physical characteristics of cuff 2 through cuff identification apparatus 42. It will be apparent that other apparatus may be used to determine whether cuff 2 encircles limb of the individual patient 4.

Patient monitor module 40 may include a physiologic sensor adapted for sensing a level of a physiologic parameter of the individual patient. In a preferred embodiment, the physiologic sensor is blood flow sensor 44 and the level of a physiologic parameter is the individual patient's Limb Occlusion Pressure (LOP), as described by McEwen in U.S. Pat. No. 9,301,701. As described in the preceding paragraph, patient monitor module 40 may automatically actuate protocol hazard key 24 if the sensed level of a physiologic parameter of the individual patient exceeds a predetermined threshold. Alternatively, patient monitor module 40 may automatically stop the safety protocol by ending the stored protocol time period if the level of physiologic parameter falls below a stored threshold. The plurality of stored pressure levels and plurality of stored times associated with the selected protocol symbol, and their safety limits may also be modified based on the measured level of a physiologic parameter of the individual patient. For an example, depending on the measured LOP value, the plurality of stored pressure levels may be LOP plus a safety margin. The safety margin may further be modified depending on the measured LOP value. Alternatively, the plurality of stored pressure levels may be a function of LOP, such as a percentage. It will be apparent that other apparatus may be used to determine a level of physiologic parameter the individual patient 4.

Figure 3:
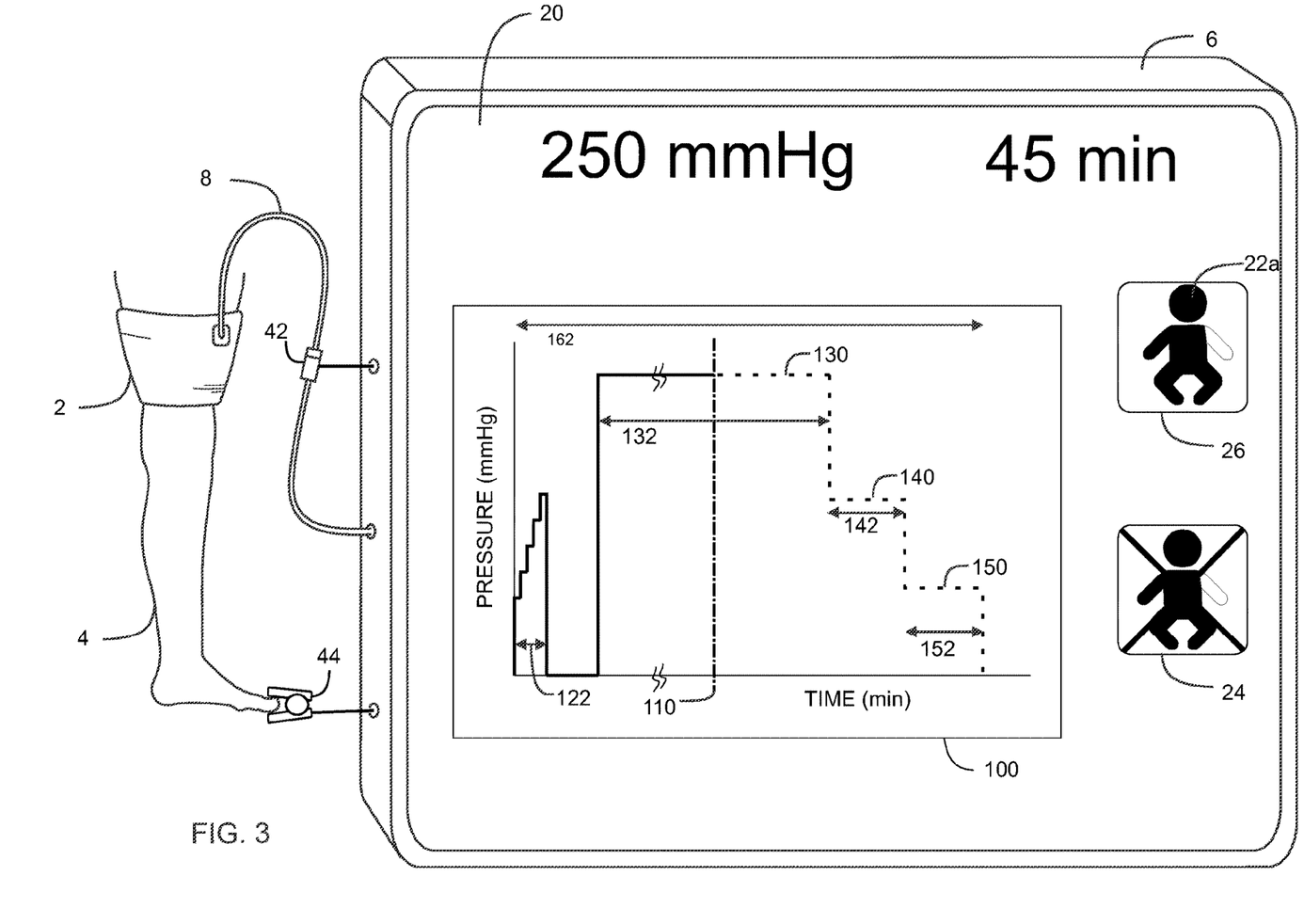
FIG. 3 is a pictorial representation of a preferred embodiment in use during surgery while a protocol symbol corresponding to a pediatric upper limb procedure is selected.

User interface 20 may include safety protocol indicator 26. While controller 10 is operable, protocol safety interlock 30 may communicate with safety protocol indicator 26 to display a user-perceptible indication that a safety protocol has been selected, as shown in FIG. 3. When the stored protocol time period ends at the end of the safety protocol, safety protocol indicator 26 is removed from the user interface and no longer perceptible by the user.

To permit the invention to be used safely for various unique patients and medical procedures, multiple unique safety protocols are stored by controller 10. Each unique safety protocol stored by controller 10 is associated with a unique symbol.

Figure 2:
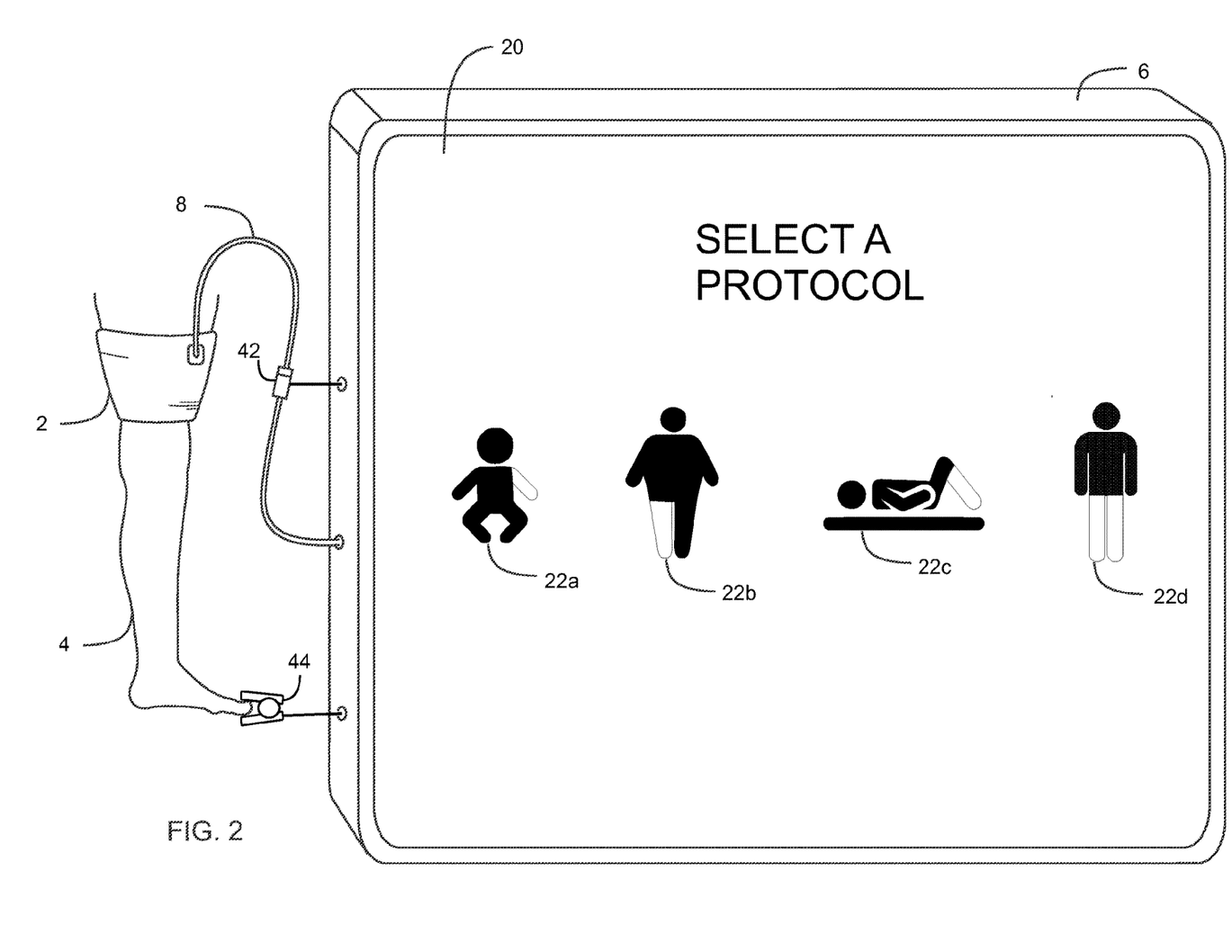
FIG. 2 is a pictorial representation of a preferred embodiment in use during surgery for selecting a protocol symbol from a plurality of protocol symbols.

FIGS. 2-3 depicts an operation of a tourniquet system of a preferred embodiment.

As shown in FIG. 2, user interface 20 displays protocol symbols 22a, 22b, 22c and 22d. Each protocol symbol is associated with a safety protocol stored by controller 10. User interface 20 allows a user of instrument 6 to select a desired safety protocol by touching the associated protocol symbol or otherwise indicating a selection.

FIG. 3 shows user interface 20 during a stored protocol time period after the user has selected protocol symbol 22a from FIG. 2. User interface 20 includes user-perceptible indication of the selected safety protocol through safety protocol indicator 26. Safety protocol indicator 26 displays selected protocol symbol 22a which is associated with a safety protocol suitable for a surgical procedure on a pediatric patient's upper limb.

User interface 20 shows the plurality of stored pressure levels and stored times throughout the stored protocol time period associated with the selected safety protocol through graphical representation 100.

In graphical representation 100, instrument 6 is at time point 110. The solid lines left of time point 110 schematically show the pressure and time profile already completed by instrument 6 according to the selected safety protocol. Firstly, an automatic LOP measurement was taken during time period 122 using blood flow sensor 44. Secondly, cuff 2 was inflated to stored pressure level 130 during time period 132 to allow the surgical procedure to be performed.

The dashed lines right of time point 110 schematically show the pressure and time profile that remains to be completed by instrument 6 according to the selected safety protocol. At the end of time period 132, instrument 6 will decrease the level of pressure in cuff 2 to stored pressure level 140 during time period 142, then to stored pressure level 150 during time period 152, and finally to a pressure level near 0 mmHg at the end of stored protocol time period 162 to allow the user to check for the release of toxins in the pediatric patient.

As an alternative to an automatic LOP measurement at the start of stored protocol time period 162, user interface 20 may prompt a user to input parameters such as the medical procedure to be performed, the patient's age, limb circumference, gender or weight, or the patient's LOP as measured manually through Ultrasound Doppler. Then controller 10 uses a predetermined formula included in the selected safety protocol to specify the stored pressure levels, times, and safety limits.

Stored pressure levels 130, 140, 150 are functions of the patient's measured LOP, as specified by the selected safety protocol. The function may be a percentage of the patient's measured LOP, the patient's measured LOP plus a safety margin or other predetermined mathematical function. The safety protocol may further adapt the stored pressure levels, times, and safe adjustment limits based on the result or the method of the LOP measurement. User interface 20 allows the user to adjust the stored pressure levels and times associated with the selected safety protocol within the safety pressure and time limits. For example, a safety protocol for upper-limb surgery of a pediatric patient may specify the first stored pressure level to be LOP plus 50 mmHg, and safety pressure limits at LOP and LOP plus 100 mmHg. If the user attempts to adjust stored pressure levels or times beyond the safety limits, controller 10 may produce a visual and/or audio alert through user interface 20 and/or speaker 50. In this example, if the user attempts to adjust the first stored pressure to be below LOP or above LOP plus 100 mmHg, controller 10 will produce a visual and/or audio alert through user interface 20 and/or speaker 50. The system may be adapted to include a second cuff and a second hose assembly. Controller 10 may be adapted to regulate pneumatic pressure near a stored pressure level for each cuff as specified by a safety protocol. All functions of the instrument and safety protocol are the same as described above, except that a safety protocol specifies stored pressure levels, times, and safety limits for both cuffs, thereby synchronizing the control of stored pressure levels in each cuff to allow safe and effective inflation and deflation of both cuffs for IVRA procedures or bilateral surgical procedures or BFR therapy.

The above invention describes a tourniquet apparatus having user-selectable safety protocols for enabling an individual user to quickly specify a safe tourniquet operation for an individual patient to facilitate a medical procedure involving the patient while simultaneously preventing operation of the tourniquet that may be hazardous to the patient.

In view of the many possible embodiments to which the disclosed principles may be applied, it should be recognized that the illustrated embodiments are only preferred examples and should not be taken as limiting in scope. Rather, the scope of protection is defined by the following claims.

We claim:

1. A tourniquet apparatus, comprising:
a cuff for encircling and applying a level of pressure to a limb of an individual patient;
a user interface adapted for selection by a user of a protocol symbol from a plurality of protocol symbols wherein each protocol symbol is indicative of a corresponding safety protocol that specifies a series of stored pressure levels, with each stored pressure level associated with a stored time during a stored protocol time period, and wherein the user interface is further adapted to enable the user to adjust at least one pressure level of the series of stored pressure levels indicated by the selected protocol symbol within safe pressure limits associated with the selected protocol symbol;
a controller responsive to the series of stored pressure levels and the associated stored times specified by the safety protocol, after any adjustments by the user, and operable during the stored protocol time period for maintaining the level of pressure applied by the cuff to the individual patient near the series of stored pressure levels for each stored time associated with the stored pressure level;
a protocol hazard key adapted for manual actuation by the user to end the stored protocol time period at any time while the controller is operable if a hazard to the individual patient is perceived by the user; and
a protocol safety interlock adapted to prevent selection of a second protocol symbol by the user while the controller is operable.

2. The apparatus of claim 1, further comprising a physiologic sensor adapted for sensing a level of a physiologic parameter of the individual patient, and further adapted for ending the stored protocol time period if the sensed level exceeds a predetermined threshold.

3. The apparatus of claim 1, further comprising a physiologic measurement apparatus adapted for measuring a Limb Occlusion Pressure of the individual patient, and wherein the protocol hazard key is further adapted for automatic actuation if the Limb Occlusion Pressure exceeds a predetermined threshold.

4. The apparatus of claim 1 wherein actuation of the protocol hazard key overrides the series of stored pressure levels with a predetermined pressure level.

5. The apparatus of claim 1 wherein the controller further stops responding to the series of stored pressure levels and the associated stored times at the end of the stored protocol time period.

6. The apparatus of claim 1 wherein the controller further replaces the series of stored pressure levels with a predetermined pressure level at the end of the stored protocol time period.

7. The apparatus of claim 1 wherein the controller further replaces the associated stored times with a predetermined time at the end of the stored protocol time period.

8. The apparatus of claim 1, wherein the controller is further operable after the end of the stored protocol time period for maintaining the level of pressure applied by the cuff to the limb of the individual patient near a predetermined pressure level.

9. The apparatus of claim 1, wherein the protocol safety interlock is further adapted to prevent selection of the second protocol symbol after the stored protocol time period ends while the cuff encircles the limb of the individual patient.

10. The apparatus of claim 1, wherein the protocol safety interlock prevents adjustment of any one of the series of stored pressure levels beyond the safe pressure limit associated with the selected protocol symbol while the controller is operable.

11. The apparatus of claim 1, wherein the protocol safety interlock prevents adjustment of any one of the associated stored times beyond a safe time limit associated with the selected protocol symbol while the controller is operable.

12. The apparatus of claim 1, wherein the user interface is further adapted to display a user-perceptible indication that the safety protocol has been selected.

13. The apparatus of claim 12, wherein the user-perceptible indication is removed from the user interface at the end of the stored protocol time period.

14. The apparatus of claim 1, wherein the safety protocol further specifies that each one of the series of stored pressure levels is a predetermined function of a measured Limb Occlusion Pressure of the individual patient.

15. The apparatus of claim 14, wherein the predetermined function of the measured Limb Occlusion Pressure of the individual patient is a percentage.

16. The apparatus of claim 1, wherein the safety protocol further specifies that each one of the series of stored pressure levels is greater than a measured Limb Occlusion Pressure of the individual patient by a predetermined margin.

17. A tourniquet apparatus, comprising:
a cuff for encircling and applying a level of pressure to a limb of an individual patient;
a user interface adapted for selection by a user of a protocol symbol from a plurality of protocol symbols wherein each protocol symbol is indicative of a corresponding safety protocol that specifies a series of stored pressure levels, with each stored pressure level associated with stored time during a stored protocol time period, and wherein the user interface is further adapted to enable the user to adjust at least one stored time indicated by the selected protocol symbol within safe time limits associated with the selected protocol symbol;
a controller responsive to the series of stored pressure levels and the associated stored times specified by the safety protocol, after any adjustments by the user, and operable during the stored protocol time period for maintaining the level of pressure applied by the cuff to the individual patient near the series of stored pressure levels for each stored time associated with the stored pressure level;
a protocol hazard key adapted for manual actuation by the user to end the stored protocol time period at any time while the controller is operable if a hazard to the individual patient; and
a protocol safety interlock adapted to prevent selection of a second protocol symbol by the user while the controller is operable.

18. A tourniquet apparatus, comprising:
a cuff for encircling and applying a level of pressure to a limb of an individual patient;
a user interface adapted for selection by a user of a protocol symbol from a plurality of protocol symbols wherein each protocol symbol is indicative of a corresponding safety protocol that specifies a series of stored pressure levels, with each stored pressure level associated with a stored time during a stored protocol time period, and wherein the user interface is further adapted to enable the user to adjust at least one pressure level of the series of stored pressure levels indicated by the selected protocol symbol within safe pressure limits associated with the selected protocol symbol;
a controller responsive to the series of stored pressure levels and associated stored times specified by the safety protocol, after any adjustments by the user, and operable during the stored protocol time period for maintaining the level of pressure applied by the cuff to the individual patient near the series of stored pressure levels for each stored time associated with the stored pressure level;
a protocol hazard key adapted for actuation by the user to manually end the stored protocol time period at any time while the controller is operable if a hazard to the individual patient is perceived by the user;
a protocol safety interlock adapted to prevent selection of a second protocol symbol by the user while the controller is operable; and
a patient monitor adapted for monitoring connection of the tourniquet apparatus to the individual patient, and wherein the tourniquet apparatus is further adapted for ending the stored protocol time period if the monitored connection to the individual patient is interrupted.

19. The apparatus of claim 18 wherein the patient monitor includes a physiologic sensor adapted for sensing a level of a physiologic parameter of the individual patient, wherein the connection is monitored by monitoring the level of the physiological parameter, and wherein interruption is determined if the level falls below a stored threshold.

* * * * *

UNITED STATES PATENT AND TRADEMARK OFFICE
CERTIFICATE OF CORRECTION

PATENT NO. : 11,944,322 B2
APPLICATION NO. : 17/252704
DATED : April 2, 2024
INVENTOR(S) : McEwen et al.

Page 1 of 1

It is certified that error appears in the above-identified patent and that said Letters Patent is hereby corrected as shown below:

In the Claims

Column 10, Line 28, "controllerfurther" should read --controller further--.

Signed and Sealed this
Twenty-second Day of October, 2024

Katherine Kelly Vidal
*Director of the United States Patent and Trademark Office*